United States Patent
Sala Meseguer

[19]

[11] Patent Number: 6,093,023
[45] Date of Patent: Jul. 25, 2000

[54] DENTAL IMPLANTS WITH EXTERNAL POLYGONAL HEAD

[76] Inventor: Juan Carlos Sala Meseguer, Paseo de Soto, 22 - 4º, 03001 Alicante, Spain

[21] Appl. No.: 09/230,132

[22] PCT Filed: Jul. 15, 1997

[86] PCT No.: PCT/ES97/00178

§ 371 Date: Feb. 24, 1999

§ 102(e) Date: Feb. 24, 1999

[87] PCT Pub. No.: WO98/03129

PCT Pub. Date: Jan. 29, 1998

[30] Foreign Application Priority Data

Jul. 18, 1996 [ES] Spain ..................................... 9601606

[51] Int. Cl.$^7$ ..................................................... A61C 8/00
[52] U.S. Cl. ................................................................ 433/173
[58] Field of Search ..................................... 433/172, 173, 433/174, 176

[56] References Cited

U.S. PATENT DOCUMENTS

| | | | |
|---|---|---|---|
| 5,338,196 | 8/1994 | Beaty et al. ......................... | 433/173 X |
| 5,759,034 | 6/1998 | Daftary .................................... | 433/173 |
| 5,779,480 | 7/1998 | Groll et al. ............................. | 433/173 |
| 5,810,592 | 9/1998 | Daftary .................................... | 433/173 |
| 5,873,722 | 2/1999 | Lazzara et al. ........................ | 433/173 |
| 5,938,443 | 8/1999 | Lazzara et al. ........................ | 433/173 |
| 5,961,328 | 10/1999 | Somborac et al. ..................... | 433/173 |

*Primary Examiner*—Nicholas D. Lucchesi
*Attorney, Agent, or Firm*—Helfgott & Karas, P.C.

[57] ABSTRACT

The invention comprises the following elements: cervico-anatomical orientation posts (FIGS. 1–8) used in the first surgical operation, in order to help replace the dental pieces to be restored; cervico-anatomical temporal healing pillars, of the direct or indirect type (FIGS. 9–12) whose design is intended to provide the gingival tissues with the morphology necessary in the healing phase and the ideal housing for the artificial tooth. Transporter (FIGS. 13 and 14), this being the element which evaluates the orientation, depth and inclination of the implants; direct and indirect cervico-anatomical transfer pins (FIGS. 16–18), which copy the exact intraoral position of the implants and the peri-implantory soft tissues; parallelizer (FIGS. 19 and 20) which replicate the position of the polygonal head of the implant; hexagonal base (FIGS. 23 and 24) for angle pillars; surgical guides (FIGS. 25–36) presenting the directing piece, patterns, tubular parts for bone drilling and direction posts.

6 Claims, 10 Drawing Sheets

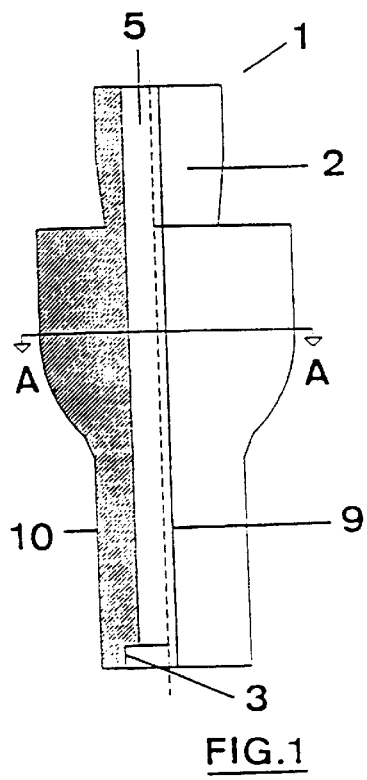
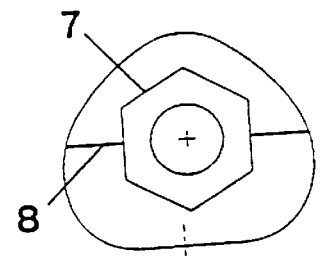
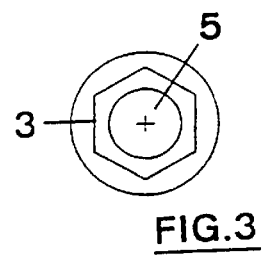
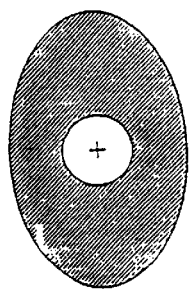
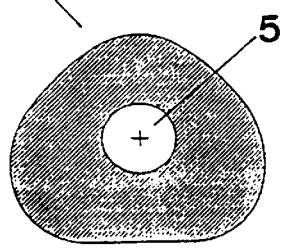
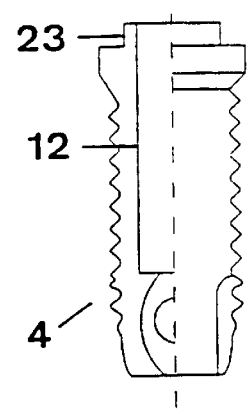
FIG.1
FIG.2
FIG.3
FIG.4
(A-A)
FIG.5
(A-A)
FIG.6

(B·B)

(B·B)

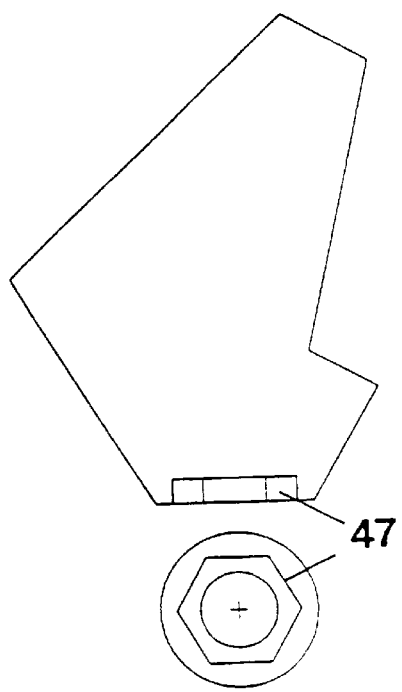
FIG. 23
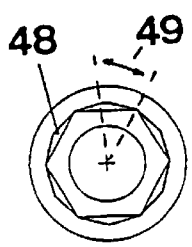
FIG. 24
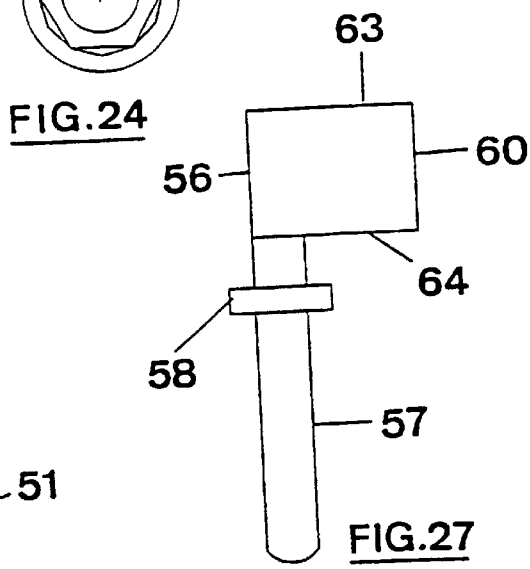
FIG. 27
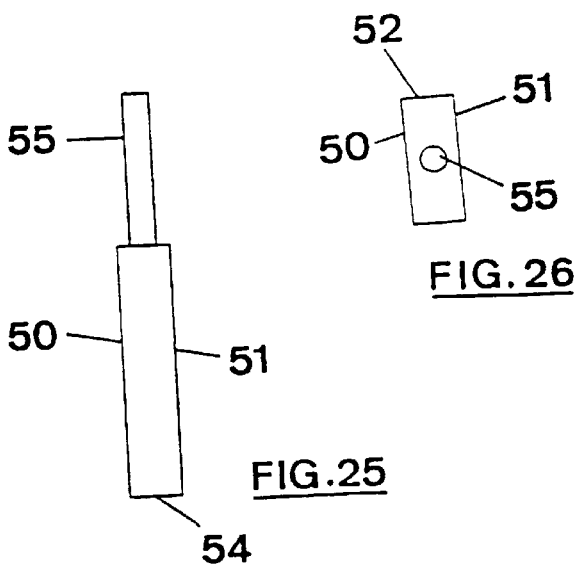
FIG. 26
FIG. 25
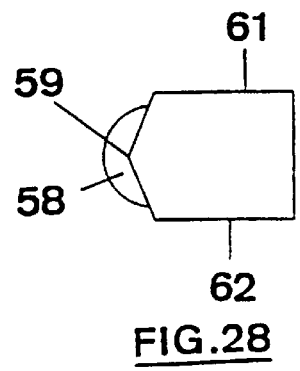
FIG. 28

DENTAL IMPLANTS WITH EXTERNAL POLYGONAL HEAD

OBJECT OF THE INVENTION

This invention according to that indicated in the title of this descriptive report consists of improvements introduced in dental implants with external polygonal head, in the field of general dental implants, where there will be fixing in the bone and a prothesic restoration, joined to each other through the gum, this resetting being reached from a single crown, to a total denture, both fixed and detachable. Specifically, the invention provides and advance in the fixing and arrangement of implants (surgical guides), as well as peri-implantary soft tissues (cervico-anatomical attachments), during the process of healing, contributing an outline as similar as possible to a natural tooth.

BACKGROUND OF THE INVENTION

For some time, many solutions have been accepted to retain in a stable manner several materials: metallic, ceramic or acrylic, supported by implants (threaded or impacted) in maxillary bones. At a primary state, all of them have been accepted by the organism, but secondary causes, derived from their surgical or prothesic handling result in an excessive closeness between them (inter-implantary gap), convergence or divergence (lack of parallelism and excessive biomechanical stresses), or non anatomical deficient gingival architecture (compromise of hygiene and food packing), which have led to inflammatory problems in the peri-implantary soft tissues (periodontal) and reduction of hard tissues (bone), with the failure and final loss of said implants. Without forgetting from the aesthetic point of view, large number of failed tests to reach a visual appearance that the user never really accepts.

One of the problems most discussed, has been the morphological discrepancy existing between fixing in the bone-implant and the root of a natural tooth; most current implants have a round or cylindrical outline in their head or upper end and non-anatomical (oval, triangular), different to what occurs in natural dentures. Attempts have been made to solve this discrepancy by using healing pillars in the second surgery. First of all, the only result obtained with these pillars was an alignment of the external outline of the implant, being externalized above the gum, for connection of the definite prothesic restoration. In this period of the implanting technique, osteointegration prevailed more than the aesthetic role of restoration.

After a time, the so-called anatomically sized healing pillars appeared (Emergence Profile System), proposed by Lazzara (U.S. Pat. No. 4,856,994), likewise by Niznick (U.S. Pat. No. 4,758,161 July, 1988; E.P. no. 0669111 AZ and B.P. No. 0669111 A3 November, 1994) propose another system of healing pillars (Spectra System), and last but not least, Daftary presented the system of anatomical pillars with successive modifications (U.S. Pat. Nos. 5,035,6319 July, 1991; 5,073,111 December, 1991; 5,145,978 September, 1992; 5,213,502 May, 1993; 5,362,235 November, 1994; 5,431,507 July, 1995; FE 2070239 July, 1995).

The principle of all these pillars is based on the expansion of the peri-implantary soft tissues, creating a sufficient space to locate an artificial tooth, with the most acceptable gingival outline, but not solving the previous premise of the original healing pillars, but contributing like the previous ones a round section at a cervical level and non-anatomical (oval, triangular) as occurs in a sectional cut at this level, in the natural denture.

To solve this problem, the fixing of healing pillars has also been proposed for their intra-oral modification, permitting, according to the operators criterion their inter-proximal, occlusal and axial reduction of their walls, proposed by Sicilia (ES 2051239), or extra-oral techniques, by means of temporary restorations to create a correct morphology in the healing of the peri-implantary soft tissues, according to the neighboring contra-lateral dentition, forming a tissue guide in the sub-gingival gap where the final prothesic restoration is going to be housed.

Highlighting the modification introduced by Daftary F., with the bio-aesthetic system (Bio-aesthetic Abutment System, *International Journal Dental Symposia*, vol. III, n1 pp. 10–15, Steri-os Yorba Linda, Calif.), in which he informed of the attainment of a transmucosal pillar of totally anatomical shape, making the use or manufacture of other types of provisional restorations unnecessary, for the peri-implantary soft tissue guide.

To obtain an optimum tissue harmony between the prothesic restoration and the implant supporting it, we should control the emergence direction of the external head of the fixing notifying that a minimum deviation exists, as an excessive inclination towards the mouth would imply an important aesthetic compromise and if the opposite occurs towards the tongue, we will cause of problem of hygienic maintenance for the user and for this reason, it should count with a system of surgical guides controlling the parallelism and gap between the successive implants and adjacent teeth during the initial drilling of the bone in the first surgery.

Currently, a controversy exists, as a result of the appearance of the surgical aid system proposed by P. Palacci (Optimal Implant positioning and soft tissue management for Branemark System, Quitossensu Publishing Company Inc. 1995) where the method is laid down and its use-discussed (R.X. Sullivan; Nobelpharma Hoy; Vol. 5 No. 1 pp. 2, 1996) to manage that the first locations for implants adjacent to natural teeth begin exactly at 3.5 mm distance, this being considered a minimum and frequently ideal for natural dentition.

For this reason, the challenge of designing a system contributing an anatomical, biological, functional and pre-determined aesthetic outline, in turn not implying restrictive handling due to its complexity for the operator, is that proposed with the system of orientation posts, healing pillars and cervico-anatomical transfer pins, with their corresponding surgical guides.

DESCRIPTION OF THE INVENTION

In general lines the improvements introduced in dental implants with external polygonal head, constituting the purpose of the invention supposes a system coupled to dental implants, detachable and being adjusted in such a way they modify the peri-implantary soft tissues, configuring an anatomical outline equal to that of natural dentition, individualizing the dental anatomy depending on the absence to be rehabilitated, moreover including the attachments and accessories to take intra-oral records and their future duplication in a work model, the system consisting of:

An accessory for the first surgery called cervico-anatomical orientation post, this accessory having an upper end with an elevation, to admit the rotation and a lower end which is coupled to the polygonal fixing head of the implant.

A hollow channel runs along the entire post housing in its-interior a fixing component, which is directly screwed inside the implant. In its middle part, the post has the shape of a simulated tooth from its neck until the equator with different measurements in mesiodistal and bucolingual sense, with reference to the tooth to be restored. Its use permits the orientation of the polygonal head of the fixing with respect to the arrangement of the dental part and its location in the maxillary or mandibular arcade.

An accessory for the following phase to osteointegration, called cervico-anatomical temporal healing pillar, is used for the guided modifications of the peri-implantary soft tissues, seeking with this pillar an emergent profile of a predetermined shape. Due to their design, these pillars have the same morphometric characteristics as the natural dentition, are easily adaptable to the implants and are a direct result of the post described above, in both shape and size. They have a lower end which couples to the implant and an upper end to house a fixing component, which is crossed by a hollow channel, being finally fixed inside the implant.

After healing of the peri-implantary gingival tissues and having obtained the stability of an anatomical, functional and aesthetic emergent profile, the print obtained in the gum is duplicated in a plaster model across the cervico-anatomical transfer pins, which equal to the accessories described above, have two open ends: one to adapt it to the implant head and the other to be crossed by a fixing component, fixing said pin directly inside the implant, maintaining the same shape and size as the healing pillar used.

Besides the components already mentioned, it also describes the transport of the polygonal head of the implant and the parallelizer, all these components being detailed below, as well as their characteristics and application techniques.

To facilitate the understanding of the characteristics of the invention, and being an integral part of this descriptive report, some plans are attached in whose figures, and with an illustrative and non-limiting character, the following are represented:

BRIEF DESCRIPTION OF THE DRAWINGS

FIG. 1. This is a view of the side elevation of a cervico-anatomical orientation post, according to the invention.

FIG. 2. This is an upper plan view of FIG. 1.

FIG. 3. This is a plan view of the lower part of that shown in FIG. 1.

FIGS. 4 and 5. These are respective sections along the cutting line A—A of the figure with an anatomical morphology corresponding to canine and premolar and incisive parts.

FIG. 6. This is a view in longitudinal elevation of an implant with polygonal head.

FIG. 23. This is a view in side and plan elevation, of a conventional angle pillar, with its modified hexagonal base.

FIG. 24. This is a view in plan of the angle pillar base, with an internal hexagonal configuration more favourable than the twelve-angled structure shown with finer plotted lines.

FIGS. 25 and 26. These are respective views in elevation and plan of the directing piece.

FIGS. 27, 28 and 29. These are respective views in elevation, plan and lower plan of the surgical pattern.

PREFERRED EMBODIMENT OF THE DESCRIPTION

Figure 7:
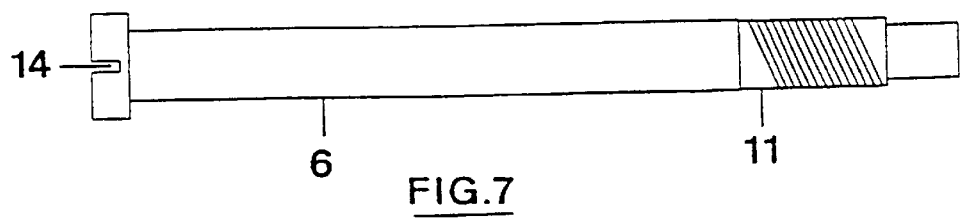
FIG. 7. This is a view of a fixing screw of the simulated artificial tooth.

Referring to the numbers adopted in the figures, we can see represented for illustrative purposes, only a reduced number of the possible embodiments of the inventions. Making special reference to FIGS. 1 to 8, the cervico-anatomical orientation post is an attachment which, for its design, improves the arrangement and housing of the dental parts to be rehabilitated, during the first surgery, covering the requirements for the following teeth, namely, central and lateral incisives (triangular), canine, first and second premolar (oval).

The post is a replica with the anatomical shape of the missing dental parts. The crown of this simulated artificial tooth 1, is made of biocompatible rigid metallic or plastic material, said posts have two open ends, an upper activated end 2 (rotation) and a lower end for its fixing 3 in the polygonal head of the implant 4. An internal hollow channel 5 runs along the post in its entire section for the passage of a fixing screw 6.

In the upper end 2, it has a polygonal, square or hexagonal elevation 7, for the embedding of a key or other mechanical device activating the rotation of the implant (⅛, ⅒, 1/12 turn) and on the surface of its upper face, said end has a reference line 8, marking its mesiodistal diameter.

This part continues towards its base, according to the body of post 1, where the simulated artificial tooth is to be found, whose anatomical morphology will depend on the absent part to be rehabilitated, having a triangular shape for incisives (see FIG. 5) and an oval shape for canines and premolars (see FIG. 4). On the vestibular surface of the post, there is a printed mark 9, indicating the longitudinal middle line of the crown. Said line coincides with the axis and polygonal vertices of the internal outline of the post in its lower end 3 and in turn, with the polygonal vertices of the external outline of the fixing head of the implant 4, when said parts are joined.

Between the post crown and its base, there is a tubular extension 10, which in its lower end has a housing with an internal polygonal outline 3, which coincides with the external polygonal outline of the implant head 4, in both size and shape.

The latter permits the anti-rotational adjustment between them. Its fixing is obtained by means of the screw 6, crossing them, said screw having a lower threaded segment 11, which screws directly to the thread 12 of the implant 4 and an upper tightening segment 14 that may be activated with the help of a screwdriver (with alien head or flat groove), hence forming an easily detachable fixed unit.

Once the size of the implant has been selected to introduce inside the bone, the post is fixed directly to the implant, fixing these components across the fixing screw 6 and the introduction of the fixing component is started with a conventional rotational instrument. Once this surgical phase is finished, the upper 8 and vestibular 9 reference lines of the post will be observed, which indicate the possible gyroversion of the simulated artificial tooth crown, with respect to the counter lateral dental parts or neighboring implants.

If said gyroversion exits or a situation unacceptable for the operator, rotation is proceeded to by means of a key embedded in the upper end elevation of the post, towards the right or left, until finding the most suitable situation.

Figure 9:
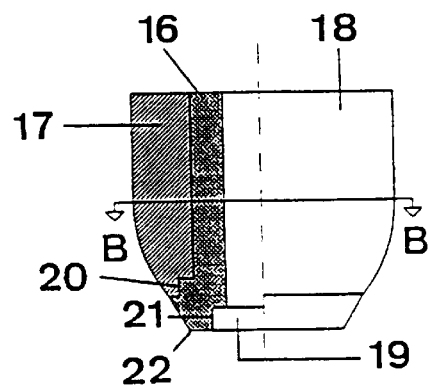
FIG. 9. This is a view in side elevation of a direct cervico-anatomical healing pillar.
Figure 15:
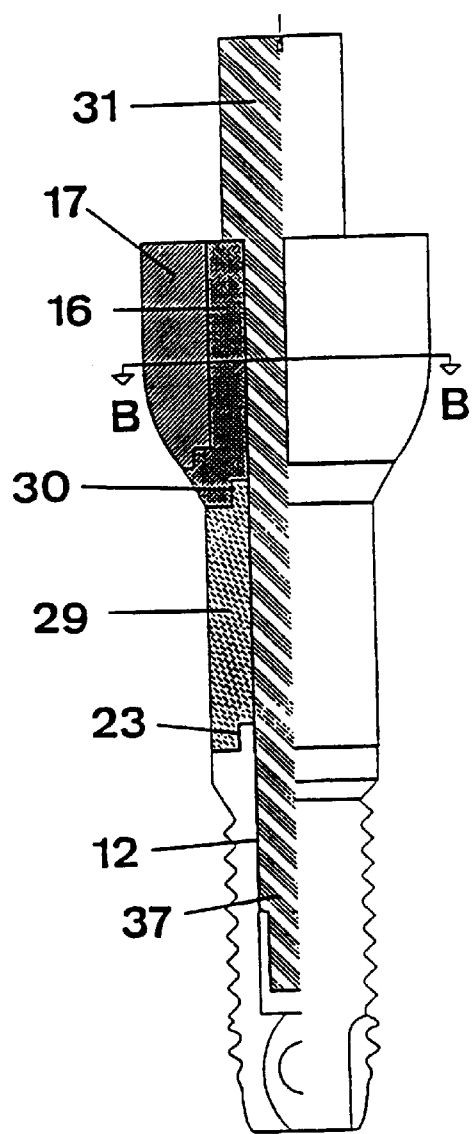
FIG. 15. This is a view in sectioned side elevation of an indirect cervico-anatomical healing pillar, used in the transporter.

Once this process has been terminated, a primary closing screw will be fitted over the implant head, awaiting its osteointegration, which occurs between 4 to 6 months, being prepared in this way for the following phase of remodeling and healing of the peri-implantary soft tissues, such that they accommodate the final prothesic restoration under the best biological, functional and aesthetic conditions, being achieved by means of the temporal healing pillars. In this invention, we will call them direct (FIG. 9) or indirect (FIG. 15) cervico-anatomical temporal healing pillars.

These are devices which as from an external round outline, like the fixing head of current implants, progressively swell into an anatomical shape upwards to obtain an emergent profile in the peri-implantary soft tissues, according to the absent tooth, following the morphometric patterns of natural dentition.

The previously proposed solutions are based on geometrically pure tronco-conical parts, which by means of mechanical handling of intra-oral or extra-oral reduction, try to create a gingival outline for the artificial tooth.

This invention avoids the aggression to the gingival tissues, due to the finish and polishing of a pre-manufactured part which provides minimum mechanization by the operator, in a space where contact with the peri-implantary soft tissues should be avoided in the possible false expectations of sealing, due to its enormous transcendence as the artificial tooth implant union interphase, which in natural dentition is called the sub-gingival gap (dental root-neck).

The cervico-anatomical temporal healing pillars described here simulated a natural tooth, where said tooth in a longitudinal cut has eliminated the portion of the clinical crown from the anatomical crown and this cut at a transverse level, coincides with the dental neck or cervix. This gap being from the neck towards its root, which is reproduced in the peri-implantary soft tissues, provides this system an accurate and not oversized adjustment between the pillar and the gum during the healing period, which we will take advantage of later on to locate, under the best conditions, the final artificial crown.

Within the cervico-anatomical temporal healing pillars we can describe two types: direct ones being the pillars used, when previously in the first surgery, cervico-anatomical orientation pillars have been used (FIG. 1), taking advantage of this circumstance, we have positioned the polygonal head of the implant in relation to the dental part to be rehabilitated and, in turn, with the neighboring counter-lateral parts, directly selecting the healing pillar which will be inserted in the implant with no or minimum modifications.

The other type of pillar, namely the indirect ones, are those which will be used when cervico-anatomical orientation pillars are not previously used.

Figure 12:
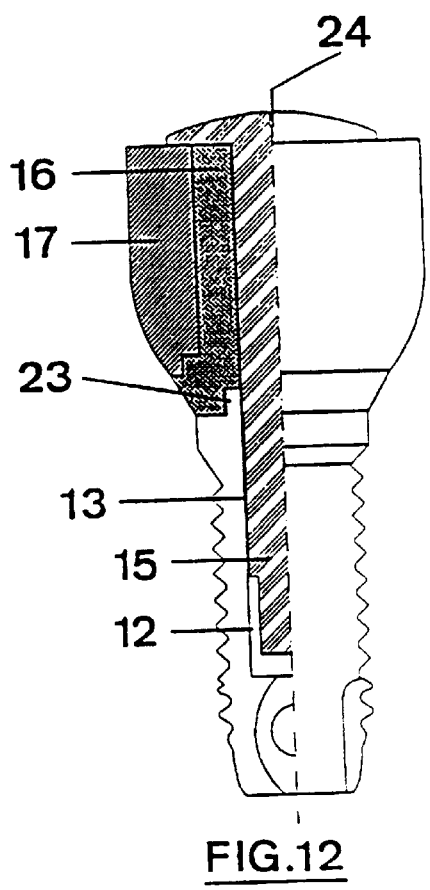
FIG. 12. This is a sectioned longitudinal view of the external anatomical body assembly with its accessories.

The direct cervico-anatomical temporal healing pillars are parts consisting of an upper end, a body and a lower end, and the entire assembly is fixed by means of a screw 13 (see FIG. 12), whose threaded part 15 is directly inserted in the threaded portion of the implant 4, the lower end and body being accessible to be assembled across the open peri-implantary tissue, both in the jaw and in the upper maxillary, during the second surgery.

Figure 10:
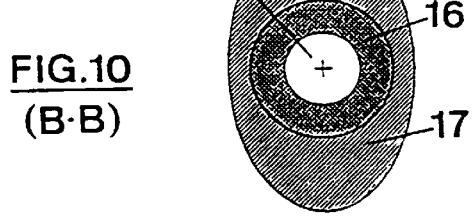
FIGS. 10 and 11. These are respective sections along the cutting line B—B of FIG. 9, depending on if it is desired to reproduce canines, first and second premolars or central and lateral incisives.
Figure 11:
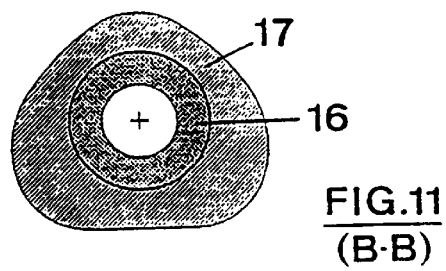
Figure 8:
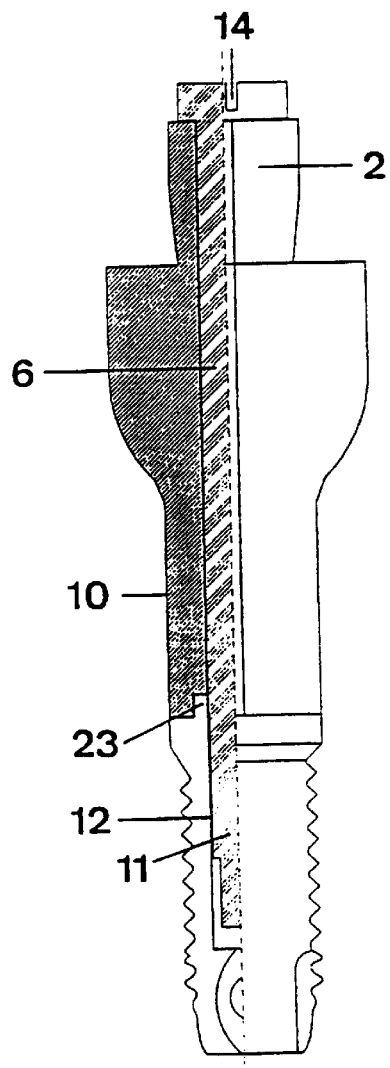
FIG. 8. This is a view of the assembly of the set of components corresponding to FIGS. 1 to 7.

Within the components integrating the pillar (FIGS. 9 to 11), we may distinguish an internal part 16 and an external anatomical body 17 that may be joined to each other forming a single unit, and which may be of biocompatible metal or rigid plastic. The internal metallic or plastic part 16, consists of a hollow cylinder with two open ends, an upper end 18 to house the fixing screw head 13 and a lower end 19 of greater diameter than the former, with a tronco-conical shape and having a single or double seating 20, the lower end of the pillar having an internal polygonal outline 21 and another external round outline 22, both coinciding with the implant head 23.

Between the upper end 18 and the lower end 19, the external anatomical body 17 is to be found, which is joined to the internal plastic metallic part 16 and surrounding it outside, its external surface being in close contact with the peri-implantary soft tissues. Predetermining the configuration of the gum and guiding said tissues in relation to the absent tooth to be rehabilitated, the axial modification of its walls may be admitted, if inter-proximal interferences of contact exist with the neighboring counter lateral teeth. The entire part in its section is hollow, for the passage of the fixing screw 13 to the implant, said screw 13 having an upper tightening segment 24 (allen or flat groove) and a lower threaded segment 15 which is directly screwed inside the implant 4.

Figure 13:
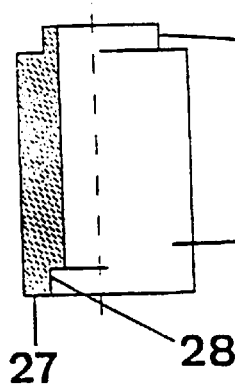
FIG. 13. This is a view in sectioned longitudinal elevation of a transporter.
Figure 14:
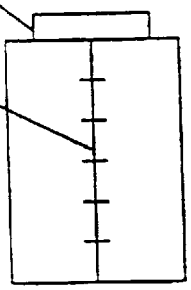
FIG. 14. This is a side view of that shown in FIG. 13.

Proceeding as follows, once the osteointegration periods have been satisfied, the primary closing screw 13, which covers the implant head is removed, proceeding to fix the direct cervico-anatomical temporal healing pillar, and for the latter the following morphometric aspects should be considered, type of orientation post employed in the first surgery, depending on the anatomy of the missing tooth, to predetermine the mesiodistal and bucolingual shape and size, which one intends to reproduce, it being possible to choose according to the following measurements for central and lateral incisives, triangular shape (FIG. 11) between 6 and 7 mm mesiodistal diameter and 5 to 6 mm bucolingual diameter, for canines; first and second premolars of an oval shape (FIG. 10), with a mesiodistal diameter of 7 to 8 mm and 5 to 6 mm bucolingual diameter. Another interesting fact is the depth from the fixing head of the implant to the free edge of the gum, a measurement which will be obtained by means of the reading in millimeters of the transporter (see FIGS. 13 and 14), the latter being an accessory to project the polygonal head of the implant upwards, evaluating the depth, orientation and inclination of the implant axis, with reference to the osseous basis of both maxillaries.

The transporter is an internally hollow cylinder of variable length (from 4 to 10 mm) being of a biocompatible rigid metallic or plastic material, with a millimetric graduation on its external surface 25, having two free ends, and upper end 26 with the replica of the external polygon of the implant head, which carries for the connection of the accessory, needed in each moment (post, pillar or transfer pin), and a lower end or base 27, with an internal polygonal housing 28 for union to the external polygonal outline of the implant head. The connection with the accessory and the transporter is made by means of a screw which is directly fixed in the implant or whatever we are using.

Regarding the indirect cervico-anatomical healing pillars (FIG. 15), they are used when in the first surgery cervico-anatomical orientation posts have not been used (FIGS. 2 to 8).

In this situation, what is intended, is to reproduce the same healing sequence, which is obtained with the direct cervico-anatomical healing pillars. In the latter, the orientation pillars are used to rotate an orientate the polygonal head of the implant in the most suitable position, depending on the position of the counter lateral dental parts or neighboring implants.

When indirect anatomical healing pillars are used, the implant is osteointegrated in the bone, without capacity for rotation and for this reason, the technique is different, the solution proposed in this invention being, first to obtain a part that may be housed in the fixing head of the implant and be antirotational. This part, described previously is the internal metallic or plastic part 16, and over it, another part which has capacity for rotation, to locate it in relation to the neighboring counter lateral parts, and which we will call the external anatomical body 17.

These two parts taken separately, different to the previous ones, do not have an active functional representation. For this reason, they should be together, obtained by means of the adhesion between them. Once this pillar is prepared in a single unit, it will be fixed to the implant by means of a fixing screw, such as the screw 13 of FIG. 12.

Once the implant and internal part are joined, an antirotational complex results, this internal part having measurements between 4 to 10 mm height, which will depend on that considered from the fixing head to the free edge of the gum.

The external anatomical body 17, will provide the anatomical outline to the healing pillar, according to the shape of the artificial tooth to be rehabilitated, being triangular for central lateral incisive and oval for canine, first and second premolars, as indicated previously. Therefore, it is the component which contributes the mesiodistal and bucolingual gap desired, during this healing period. On its vestibular phase, it has a mark on its middle line to manufacture the indirect transfer pins. The external anatomical body is of a biocompatible rigid plastic material, permitting its axial reduction if necessary. The measurement of the external anatomical body 17 vary from 4 to 10 mm depending on the height of the internal metallic or plastic part 16 chosen.

Two methods exist to prepare the indirect anatomical temporal healing pillars:

Intraoral: Directly (FIG. 15) over the fixing head of the implant, a transporter 29 is fitted, obtaining the depth of the implant head to the gingival edge, a measurement which will be used to select the pillar height. Then, an internal metallic or plastic part 16 is coupled to the upper end of the protractor 30 and over said part, the external anatomical body 17. This assembly is fixed by means of a screw 31, which is fitted directly on the implant, once the body 17 has been orientated in relation to the neighboring counter lateral teeth or implants. Lastly, both the internal metallic or plastic part 16 and the external anatomical body 17 are joined by means of an adhesive. Finally, the screw 31 is removed, extracting the transporter 29 and separating the healing pillar, the assembly being ready for placing in the mouth.

Extraoral: Indirectly by means of conventional print taking, the previous steps are followed over a plaster model. Once the indirect cervico-anatomical temporal healing pillar has been prepared, only the implant needs to be fitted to it, by means of a fixing screw with an upper tightening end and another lower threaded end, which is screwed directly inside the implant.

After six to eight weeks from fixing the cervico-anatomical temporal healing pillars, the periodontal tissues will be prepared to take an impression.

By means of the transfer pins, the position of the fixing head of the implant will be duplicated in a plaster model, and the progressive mesiodistal and bucolingual width of the peri-implantary soft tissues obtained by means of the pillars during the healing period, from the implant head to the gingival edge of the gum will be attempted, seeking the visual reality of the emergent profile in an artificial tooth, similar to that of a natural root.

The cervico-anatomical transfer pins may be divided according to the healing technique used in the second surgery. If direct healing pillars have been used, direct transfer pins will correspond and if, indirect healing pillars were used, indirect transfer pins will be relevant.

Figure 16:
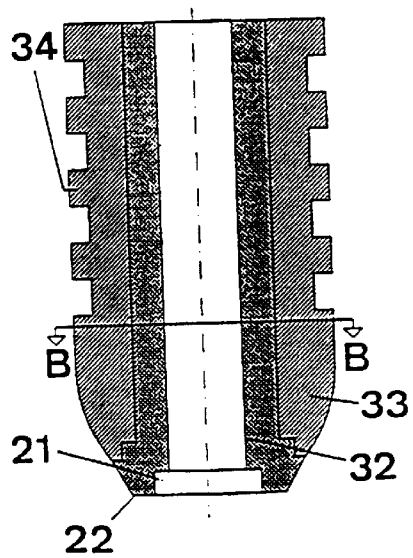
FIG. 16. This is a view in sectioned side elevation of a direct cervico-anatomical transfer pin.
Figure 17:
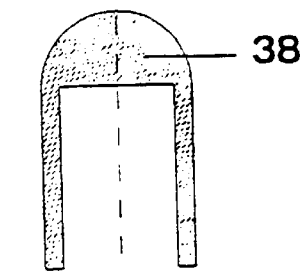
FIG. 17. This is a view in longitudinal elevation of the fixing screw and its protection head, for assembly in the transfer pin of FIG. 16.
Figure 17:
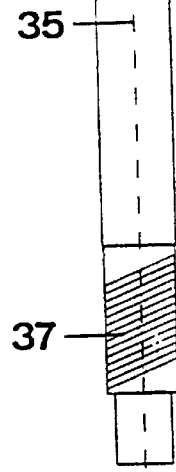
Figure 18:
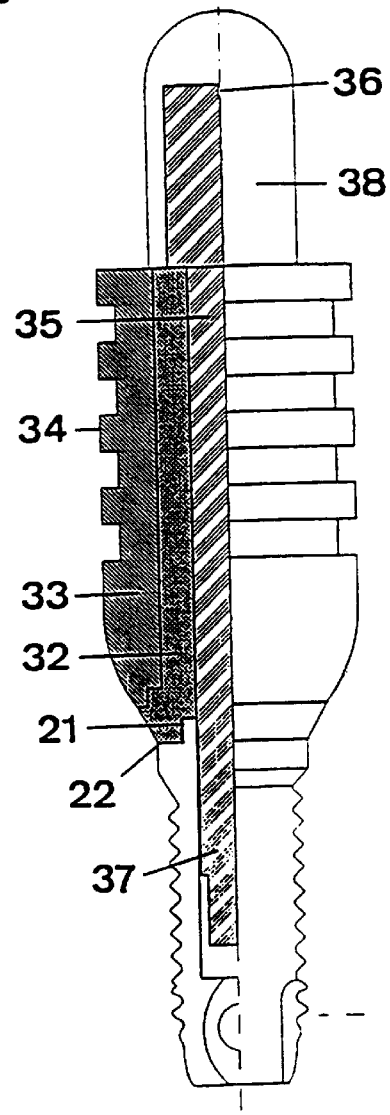
FIG. 18. This is a view in side elevation of the same direct cervico-anatomical transfer pin of FIG. 14 with all its accessories.

The direct cervico-anatomical transfer pins (FIGS. 16 to 18), will be used once the peri-implantary soft tissues have stabilized and have a height of 10 to 15 mm and a mesio-distal and bucolingual diameter compatible with the direct cervico-anatomical temporal healing pillar used. They consists of an internal metallic or plastic part 32, which at its lower end has an internal polygonal outline, and another external rounded end of diameters coinciding with those of the fixing head of the implant, previously mentioned, and an external anatomical body 33 with the same morphological characteristics as those indicated above, being triangular for incisives and oval for canines and premolars. Being different in its total height, which is greater, and in a series of retentions 34, in its central-upper segment for the anchoring of impression pastes, favoring the stability of the pin and its reliability in the implant position with reference to its intraoral location. This complex is fixed to the implant by means of a fixing screw or guide 35, with an upper tightening end 36 and a lower threaded end 37, which in the moment of impression has a detachable plastic cap 38 adapted to locate the head of the screw rapidly and to avoid the entrance of impression material in its groove.

Figures 19, 20:
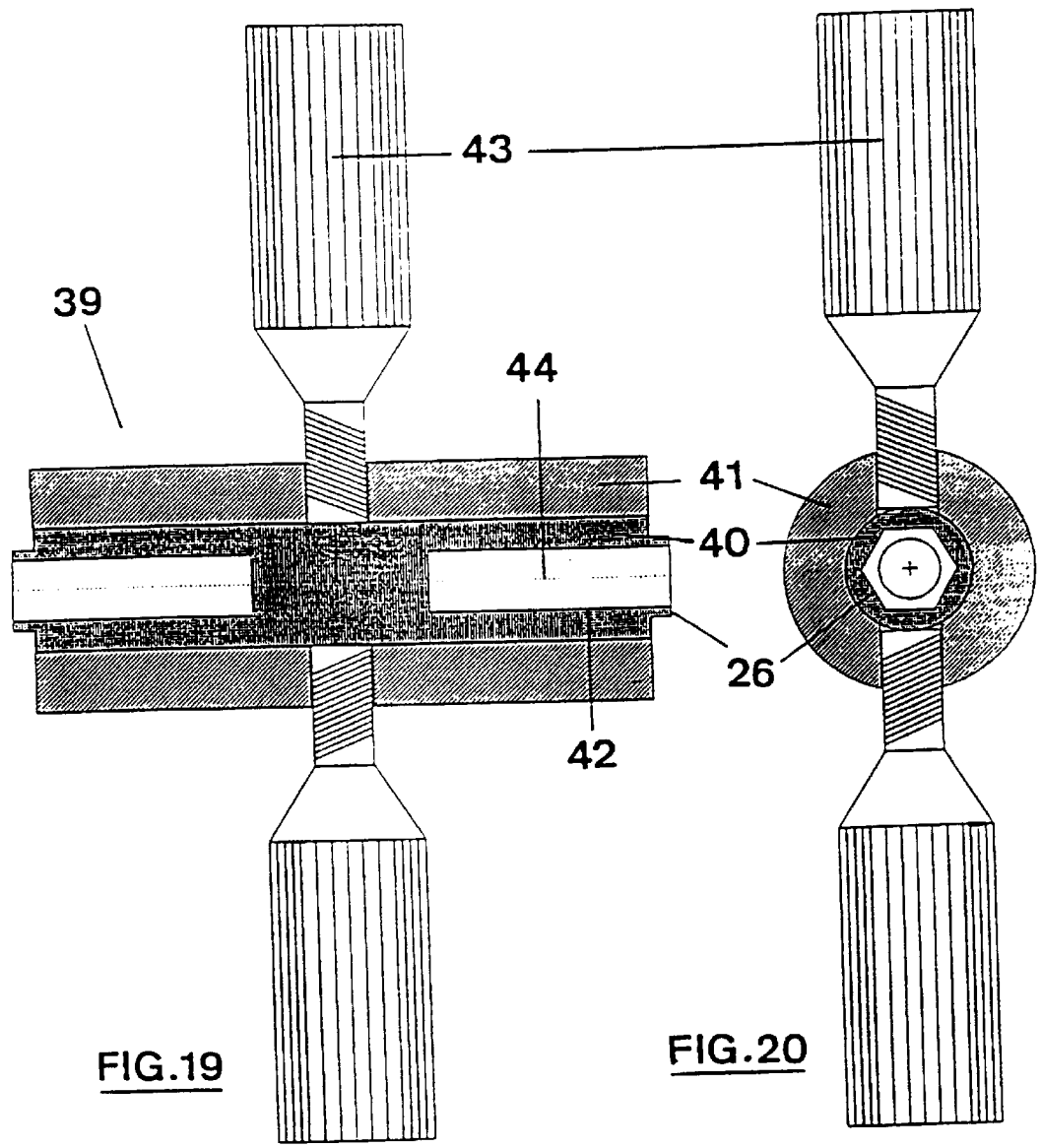
FIGS. 19 and 20. These are respective views in elevation and side elevation of a parallelizer with all its accessories.

The indirect cervico-anatomical transfer pins are used when in the second surgery indirect healing pillars are employed, these pins being compatible in shape, orientation and size, hence obtaining the parallel manufacture of both parts, pillar and pin at the same time. The components necessary for the construction of the indirect cervico-anatomical transfer pin are: the indirect cervico-anatomical healing pillar, a parallelizer 39 (FIGS. 19 and 20), an internal metallic or plastic part of the pin, similar to that numbered with 32 in FIG. 16 and an internal anatomical body of the pin, analogous to 33 in the same figure.

The parallelizer 39 may be made of biocompatible plastic or metallic material consisting of two bodies: an internal one 40 and an external one 41, the first of which is a hollow cylindrical structure, with two polygonal ends in each one of them, these being an exact replica of the external polygon of the implant head, with an internal thread 42 to fix a screw. The external body 41 is a hollow cylindrical tube, which is introduced and adjusted within the internal body 40 with capacity for rotation over the former and possibility of blockage by means of external two external keep screws 43. The surface of this body is crossed by a linear mark of reference 44 to be able to duplicate in the same position, the indirect cervico-anatomical healing pillar with the indirect cervico-anatomical transfer pin.

The internal plastic metallic part of the indirect transfer pin consists of a hollow cylinder with two open ends, an upper end and another lower end, base, the latter having a diameter greater than the former, with an inverted tronco-conical shape, with an internal polygonal end and another external end fixing in either end of the parallelizer 39 with a total height varying from 10 to 15 mm.

As we have already described, the external anatomical body 33 of the indirect transfer pin is the part providing the mesiodistal and bucolingual dimensions, being triangular for incisives and oval for canines and premolars. It consists of two open ends, an upper end and a lower end, which adjust perfectly with the internal metallic or plastic part 32. On its vestibular face, it has an engraved mark 45 indicating the middle line along its entire length. The height of this part varies from 10 to 15 mm and its diameter in relation to the artificial tooth to be replaced.

Figures 21, 22:
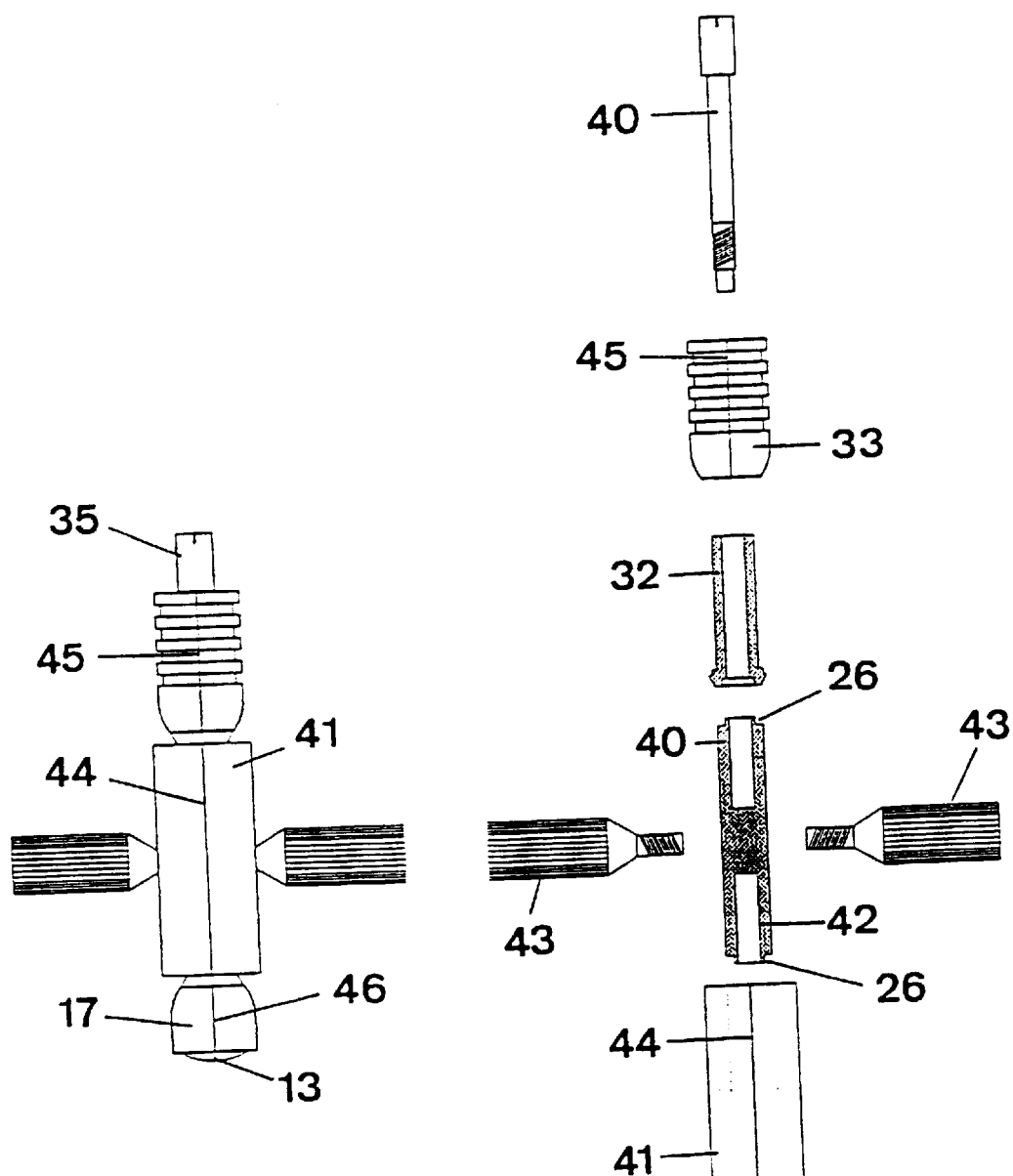
FIG. 21. This is a view in side elevation with the parallelizer parts, the transfer pins and the indirect cervico-anatomical healing pillar assembled.
FIG. 22. This is an exploded view of all the components comprising FIG. 21.
Figure 29:
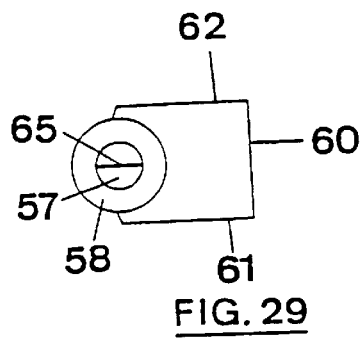

Once the indirect cervico-anatomical healing pillar has been prepared (FIG. 15) as described above, the construction of the indirect cervico-anatomical transfer pin is started (FIGS. 21 and 22). The indirect cervico-anatomical healing pillar is fixed by means of a screw 13 to one of the ends of the internal body 40 of the parallelizer 39 and then, the external body 41 is introduced over the internal body 40, making the middle marking line 44 coincide with the external body 41 of the parallelizer 39 with the middle vestibular marking line 46 of the indirect cervico-anatomical healing pillar 17 and when these coincide the internal and external body of the parallelizer are fixed by means of the two keep screws 43 located in the external body of the parallelizer.

In the other end of the parallelizer, the following parts are fixed in this order: first the internal metallic or plastic part of the indirect pin 32 is fixed, then the external anatomical body of the pin 33, rotating this until coinciding with the middle line 44 of the external body 41 of the parallelizer 39. Once the middle line 46 of the indirect cervico-anatomic healing pillar coincides with the middle line 44 of the parallelizer and it is with the middle line 45 of the external anatomical body 33 of the transfer pin, joining both to each other, by means of an adhesive forming a single unit, both the part 32 and the body 33 remain so prepared for their use to taken an impression by means of their direct fixing to the implant by a screw 35.

On certain occasions during the surgical operation, anatomical conditions occur especially in the upper maxillary which in searching for a correct osseous cover round the implant for good osteointegration, the user is obliged to incline the implant in the bucolingual direction. When later on, the prothesic idea is considered, a disadvantage arises regarding the inclination of the implant axis, which presents an unsuitable angle with respect to the osseous base and hence, the screw which is going to join the prothesis to the implant is located in a gap where it should not be.

The conditioners presented in this situation, have led the manufacturers of these tools to prepare twelve sided angled pillars, or also known as stars of twelve points, which provide twelve different fixed directions. Although in this way this system basically solves the antirotational mechanical problem, this alternative of twelve faces is necessary because the angled pillar is designed in a single part, without free axial capacity of rotation, with a rotation limited to a maximum of 30°. Therefore, the fastening is made by seeking the most relevant position of the twelve sided configuration of the pillar randomly with respect to the external hexagon of the fixing device which, sometimes is not the most optimum.

In FIG. 23 the profile of a conventional angle pillar is shown, which is not the purpose of the invention of this patent, but we would like to call attention to the internal hexagonal base 47, which may be made if previously in the first surgery during the installation of the implant, the cervico-anatomical orientation posts were used (FIGS. 1 to 8), hence obtaining a correct location of the external hexagon as has already been described.

If this situation occurs, once the external hexagon has been orientated, the base of the angle pillar may have an internal hexagonal configuration 47, obtaining a housing of mechanical antirotational effect, with more favourable characteristics than the twelve sided structure, avoiding dead spaces 48 which are created between a twelve sided figure and a hexagon, with no mechanical benefit, and also possible injuries or fractures of the external vertices of the implant hexagon and in turn, to substantially reduce the angle of 30 degrees produced by the twelve sided FIG. 49 of the current angled pillars, considerably improving the prothesic expectations.

For this reason, the solution presented here is proposed for the bases of angled pillars, independent from the angle they have with an internal hexagonal geometric configuration provided that the implants are previously orientated by means of the orientation posts (FIGS. 1 to 8).

Of all that described above, little or no relevance can it have if during the first surgery there is not a reliable measurement and parallelism method available between implants and remaining neighboring parts. If from the outset, the orientation posts permit the external polygonal head of the implant to be referenced and well situated in the maxillary or the jaw bone, the surgical guides are firstly designed to adequately plan the necessary fixing depending on the anatomical space available and on the moment of the surgical action to facilitate parallelism, hence avoiding convergences or divergences in the implant positions. In this way, a suitable distribution of biochemecanical occluding loads is obtained and safeguarding the physico-biological gap, which should exist inside the maxillary bones, between implants and adjacent dental roots, hence adequating sufficient space to house the prothesic restoration with functional and aesthetic guarantee.

The basis of this invention is the modification of the rotational instruments (round drill) and the use of other devices like the tubular retainer, which allows the bull drills and the surgical spiral of 2 mm to be directly supported over the following attachments, which from now onwards we will call ? part and surgical patterns. In this way a smooth sliding of the drills is obtained when perforation of the bone is being made, without loosing control of the parallelism, inclination and orientation of the drills.

The previous proposals to solve this problem give solutions which are more theoretical than practical, indicating below a series of advantages to be considered depending on the conditioners each specific case may present.

Firstly, the directing piece proposed here, provides the starting point of the initial fixing, managing that the first sites adjacent to the natural teeth start exactly at 3.5 mm or even less, depending on the characteristics of the case, contributing the minimum distance and frequently the ideal one in natural dentition. The directing piece plans over the study model the ideal place for perforation and intraorally guides the result of this programmed goal.

The tubular retainers permit the surgical drills (round and of 2 mm), to be constantly in contact whilst they rotate over the contact surface, both of the directing piece and the surgical patterns without ever loosing parallelism, direction or programmed distance and above all avoids the displacement of the parts, due to the rotation effect, these aspects being different as compared to other similar methods of current use.

The surgical patterns assists, according to the circumstances of the case, the selection with real precision of the distance between implants and over adjacent teeth, as well as, according to the anatomical space available, to use implants of a different diameter and to adjust them to the pattern necessary in each moment, obtaining in turn, a controlled parallelism independent from the bucolingual inclination adopted by the surgical drills, minimizing the anatomical limitations which may arise as much as possible.

Finally, the situation of the patterns over the bone is organized consecutively, visualizing the definite position of the programmed implant before their definite installation, thanks to the tolerance of 0.5 mm existing between the different surgical patterns.

The directing piece is an attachment which is used to make the first fixing base in the bone. The parallel attaintment of the following fixing depends on this part, as well as the distance between them, which has previously been ascertained and indicated on the plaster model. The material used for its preparation is preferably biocompatible rigid metal or plastic, which is adhered to the surgical acrylic ferule, its use covering the necessities for a unite planning or for several implants.

Its shape (FIGS. 25 and 26) is similar to that of a prism where six faces are identified: near or mesial 50, far or distal 51, which will be that of contact, internal or lingual 52, external or buccal 53, lower or basal 54 and upper. This latter with a shank 55 upwards for gripping and its measurements may vary from 1.5 to 5 mm, from its mesial face to its distal face, which will be according to the distance of separation between the first implant and the adjacent tooth and from 5 to 6 mm. from its external face to the internal face, with the height of 4 to 10 mm, from its lower face to the upper face. All the latter depending on the characteristics of the case may admit this piece to be reduced for a better adjustment.

The surgical pattern is a biocompatible metal or plastic part (FIGS. 27 and 28) in which two parts may be distinguished: an upper part 56, located above the bone and a lower one 57, introduced inside the bone. These two parts are divided by a disk 58. The upper part has a rectangular shape, having a mesial edge 59, distal face 60, buccal face 62, lingual face 61, upper face 63 and a lower face 64, with a measurement of 5 to 6 mm thickness between its lingual 61 and buccal 62 faces, and 5 mm height between its lower face 64 and its upper face 63; its near or mesial end 59 finishes in an arrow head with an angle of 40–60° and the far or distal end completely flat, this being the contact surface for the support of the inactive tubular retainer 66, for the ball and 2 mm drills, respectively. Between the upper part 56 and the disk 58 there is a space of 2 mm, preventing the contact of the pattern with the osseous crest and facilitating the consecutive order the patterns, one adjacent to the other without interference between them.

Figures 30, 31:
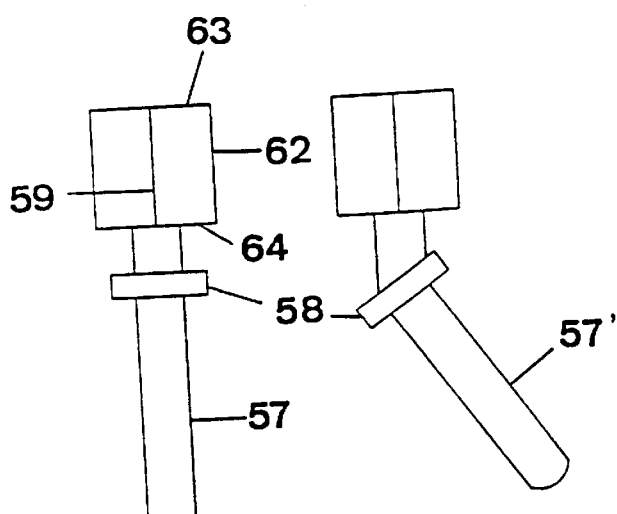
FIGS. 30 and 31. These are respective views in side elevation of the surgical pattern of FIGS. 27 to 29 of straight axis and another with an axis foreseen for a certain angle.
Figure 32:
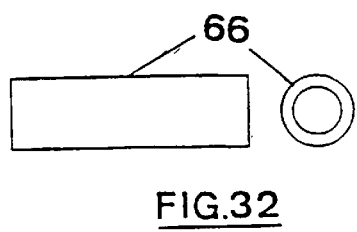
FIG. 32. These are two views in side elevation of a tubular retainer.

Beneath the disk 58, there is an axis 57 from 7 to 10 mm long and with a diameter of 2–3 mm, which is introduced in the osseous base made with the surgical drill of 2–3 mm. This axis may also present a voidance 571 (FIG. 31) from 15°–35° in buccal 62, lingual 61 direction. This axis has a central tolerance groove 65. The measurement of the surgical pattern may vary depending on the needs of the space available. Its size is contemplated from the mesial face 59 to the distal face 60, and this distance may vary from 6.5 mm to 10.5 mm in intervals of 1 mm, depending on the anatomical gap to be covered, the number of implants and their diameter, their minimum from center to center of the fixings being 7 mm and their maximum 12 mm.

Figures 33, 34:
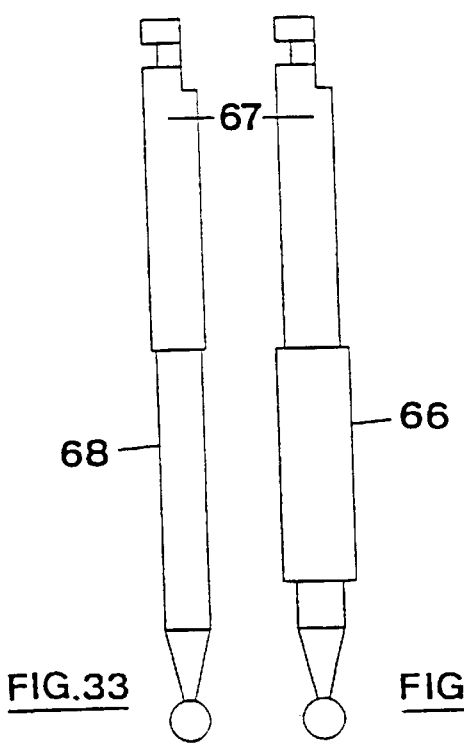
FIG. 33. This is a view in elevation of a conventional ball drill, with the shank modified permitting entrance in the tubular retainers of FIG. 32.
FIG. 34. This is a view of the same ball drill as FIG. 33, with a tubular retainer installed in the shank.

The tubular retainers 32 are parts of a hollow cylindrical shape 66 with an inside diameter of 2–3 mm and an outside diameter of 4 mm, with a height of 6 to 12 mm, of metallic material (magnetized or not), or biocompatible rigid plastic. This sleeve is placed over the ball drills 67 (FIGS. 33 and 34) and conventional 2 mm. Its function is to produce a sliding over the contact surface of the directing piece and the surgical pattern, preventing the displacement of the latter, due to the rotational effect of the cutting coils.

Figures 35, 36:
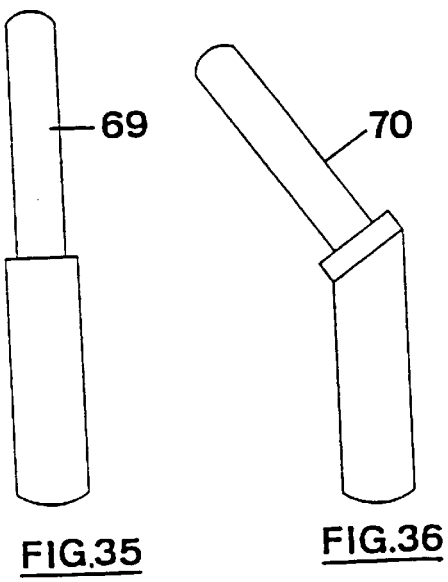
FIG. 35. This is a view in elevation of a straight surgical direction post.
FIG. 36. This is a view in elevation of an angled direction post.

Regarding the ball drill 67, the shank 68 has been modified and this modification permits the entrance of the tubular retainers 66. Finally, this system also counts with the straight surgical direction posts 69 (FIG. 35), consisting of a cylinder with one end of 2 mm and the other of 3 mm, with a length between 15 and 30 mm. Moreover, the angled direction posts 70 (FIG. 36) are also described, having equal length and diameter, being distinguished from the previous ones in the formation of an angle between 15°–30, its design allowing the control of direction, inclination and parallelism of drilling in the maxillary or mandibular bone.

The clinical procedure is as follows:

Plaster model: the number of fixtures the case requires is previously planned in an articulator mounted in the model and then (FIGS. 37a and 37b) the model is placed in a dental laboratory parallelizer (A). Once the latter has been parallelized, the shank of the directing piece 55 is introduced in the clamp of the parallelizer arm, installing the mesial wall of the part 50 over the distal wall of the tooth nearest to the first fixture, leaving the gap which is determined later on (1.5 mm or 5 mm) after preparing the acrylic ferule, including the directing piece (B) in it.

In this phase, what is being achieved is to parallelize one plane to the distal reference face of the tooth nearest to the first fixture. For the latter, the tooth axis, radicular position according to X-rays or any other occluding circumstance may be taken as a reference. The surgical procedure is as follows:

Installation of the ferule in the mount, making sure that it adjust and does not move. Over the installed ferule (C), one starts with the marking or modified ball drill 67 or introducing over it a tubular retainer 66. Immediately afterwards (see phase D) the conventional 2 mm drill 71 with its corresponding retainer 66, once the first base has been prepared, which will have 2 mm diameter and 7 to 10 mm depth inside the bone, the inclination, position and parallelism (see position E), is checked by means of the surgical direction posts 69, then, depending on the schedule of the case, installing as many successive patterns as the number and distances of the fixtures which has been decided in the initial diagnosis.

To obtain a distance of 7 mm from center to center of the implant heads, as shown in phase (F) of this figure, a pattern of 6.6 mm is used and with a tubular retainer of 2 mm internal diameter and 3 mm external diameter.

To obtain 9 mm (in position G), a pattern of 8.5 mm is used together with a tubular retainer of 2 mm internal diameter and 3 mm external diameter.

To obtain 12 mm, we shall use (see position H), a pattern of 11.5 mm and a tubular retainer of 2 mm internal diameter and 3 mm external diameter.

Figure 37A:
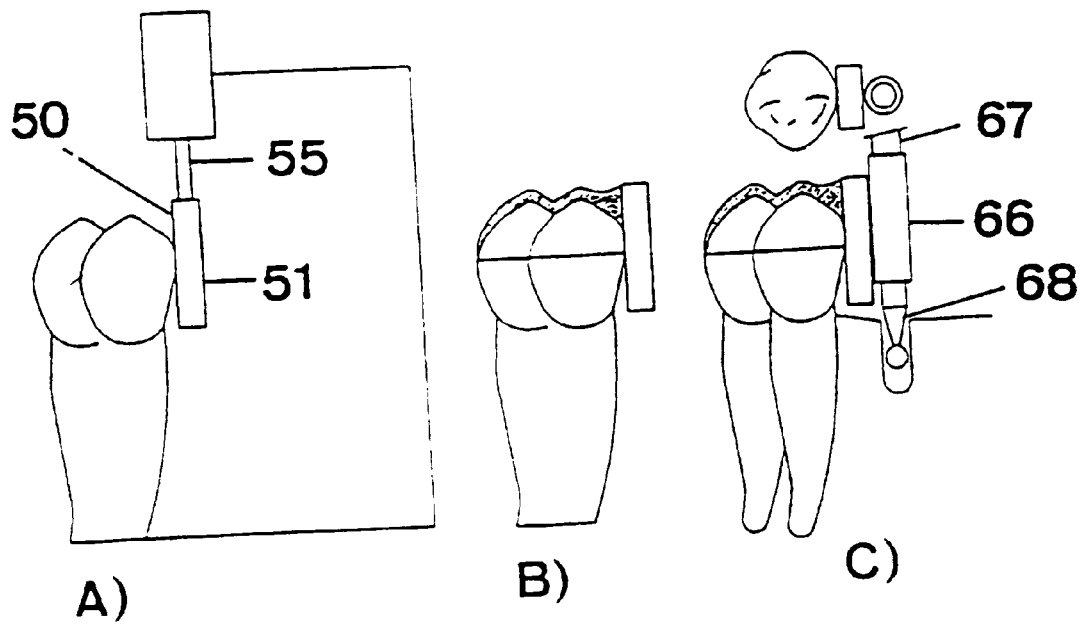
FIGS. 37a and 37b. These are a result of the clinical procedure used: phases A to H.
Figure 37A:
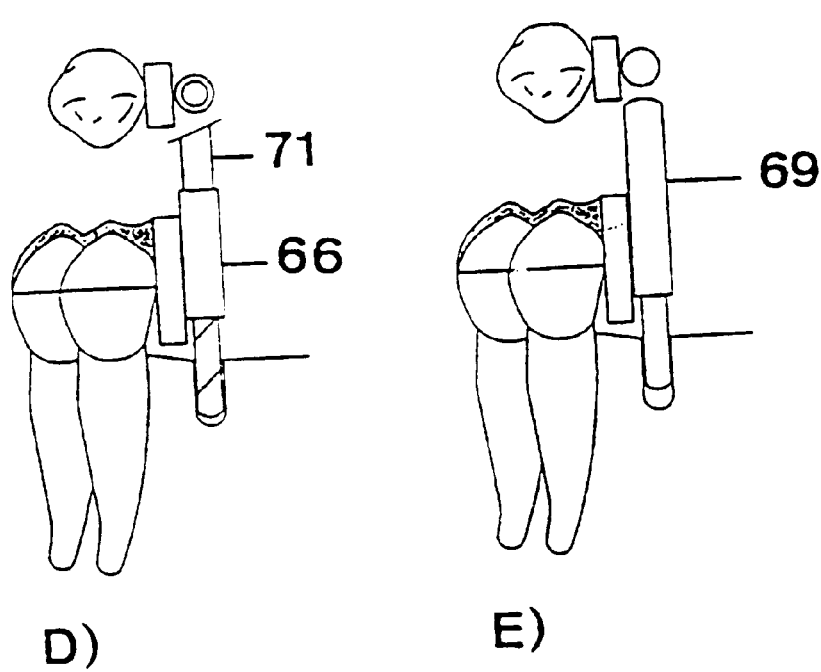
Figure 37B:
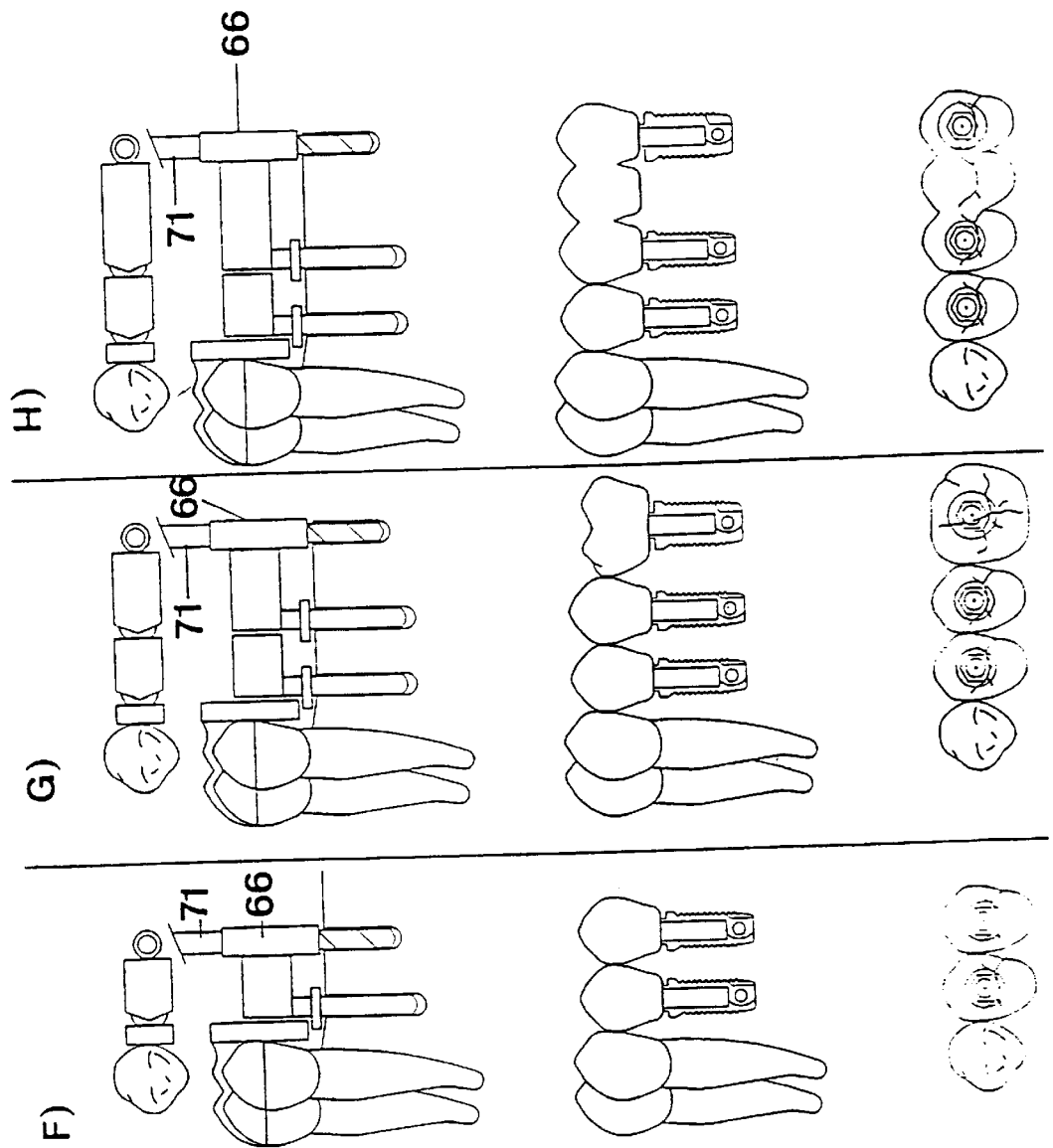

In this way, sequences shown in FIGS. 37a and 37b, the necessary perforations are planned to later drill the bone with increasing diameters until reaching the final diameter of the programmed implant. In this initial phase, there is a reliable control of distance between the successive implants and the adjacent teeth, it being possible to use six patterns of different sizes, which partially minimize the possible anatomical conditioners of the sites, which in the previous diagnostic explorations of image, could be favorable and which afterwards in the first surgery on the bone are not very feasible.

The ordered use of the patterns, before the definite installation of the implants, may be performed thanks to the use of tubular retainers which leave a gap between a directing piece and the patterns of 0.5 mm. independent from their size, in this way obtaining a real and complete view of the future position of the implants, both in the maxillary and in the jaw bone.

The clinico-surgical procedure detailed above (FIG. 37) assumes that the osseous bases are aligned or perpendicular to the adjacent teeth, but in some circumstances and especially in the front area of the upper maxillary, two aspects occur and should be taken into account: on the one hand the aesthetics and the radicular angle caused by the profile of the bone itself, on the other. For this reason, under determined circumstances of repair of a part, the operator seeks the best cleanliness of the implant, sometimes interfering with the anatomical limitation of this area to solve this situation and to find a correct bone cover around the implant with a greater osteointegration the perforation should be angled.

This condition provokes two alternatives in the prothesic phase. On the one hand, the union of the screw between the implant and the prothesis it holds emerges buccally, causing an ugly aesthetic solution or lingually causing a problem of hygienic maintenance for the user.

In the previous diagnosis, sometimes through X-ray images, and espeificaly by means of tomographies, it is reckoned that in determined areas, the possibility of installing implants irremediably involves their angling with respect to the adjacent teeth and the osseous bases, both of the maxillary and of the jaw bone.

The use of angled surgical direction posts (70) (FIG. 36) permits the objective measurements of the angling desired and which in the moment of intervention we find. In the case of a single implant, the problem would be solved, but most patients do not have a single treatment but multiple implants, some of them being angled and others not. In this case the use of surgical patterns can be resorted to with the axis 57' modified between 15° and 35°, depending on the deviation or inclination indicated by the angled orientation post 70. The function of these patterns 57' is to correct said angling to be able to obtain in the following perforation a direction as perpendicular to the bone as possible and not angled.

Therefore, it may be gradually combined with the modified axis 57' or not 57, depending on the previous information obtained in the planning of the initial diagnosis and the direction the angled direction posts 70 indicate.

And as final note, currently when an operator informs about the need or not to use an angled pillar for the final prothesis, whether a single crown or combined bridge, his information is based on the change of direction the remaining conventional posts indicate to him with respect to the adjacent teeth or the occlusion (antagonist teeth), but limiting the knowledge of the inclination degree. The method hereby described to evaluate the inclination degree of the angled pillar, which is going to support the definite prothesis is executed as follows:

After the required months of osteointegration, the second surgery is performed, installing the primary healing pillars. Some weeks are required for healing and then an impression is taken, not being definitive and merely preprothesic. Over this plaster model, a replica is checked to determined which definite pillar has the most favourable angle (according to the supplier between 15° and 30°). Later, another surgical operation is made on the patient to fit the previously chosen definite angled pillar, followed by another healing period and some weeks later, to take the definite impression. All this schedule may be simplified if during the first surgery when the bone is being perforated, the possibility exist of using the angled direction posts 70 and the angle is calibrated according to what is being drilled.

What is claimed is:

1. A system for use with dental implants having an external polygonal head consisting of anatomical components coupled to said dental implants which are adjustable and detachable comprising:

a) a tubular accessory consisting of a cervico-anatomical orientation post (1) having an upper polygonal end (2) adapted for rotation and a lower polygonal end for coupling to said polygonal head of said implant (4), b) a cervico-anatomical temporal healing pillar for the guided modification of peri-implantary soft tissues being fastenable to said implant (4) by a fixing component (13) which extends through said cervico-anatomical temporal healing pillar and into said implant, c) an indirect anatomical healing pillar for use when said implant is osteointegrated in bone, defined by a non-rotatable first part adapted for attachment to said implant and a rotatable second part adapted for attachment to said non-rotatable first part said first and second parts of said indirect anatomical healing pillar being fastenable by a threaded screw to said implant, d) a hollow, cylindrical transporter fastenable to said said polygonal head of said implant having a millimetric graduation on its longitudinal exterior line, an upper end (26) similar in appearance to that of said implant head (4) and a lower end (28) adapted for attachment to said implant, e) a direct cervico-anatmoical transfer pin comprising a tubular part (32) having an internal polygonal outline at one end which is adapted for attachment to said implant and surrounded by an external anatomical body (33) having a series of annular protrusions (34) for retaining and anchoring impression pastes, said direct cervico-anatomical transfer pin being fastenable to said implant by a fixing screw (35) having an external head adapted to be covered by a detachable cap (38) at the time of impression, f) an indirect cervico-anatomical transfer pin for use when indirect healing pillars are used, comprising an indirect cervico-anatomical healing pillar, a parallelizer (39), an internal part of said indirect cervico-anatomical transfer pin and an external anatomical body of said indirect cervico-anatomical transfer pin, g) an internal hexagonal base (47) for use with angled pillars when cervico-anatomical orientation posts (1) are used for the installation of said implant, and h) surgical guides comprising a directing piece, surgical patterns, tubular parts for drilling and direction posts.

2. A system according to claim 1, wherein said parallelizer comprises an external body (41) and an internal body (41) having a cylindrical hollow structure with two polygonal ends adapted for mating engagement with said implant head and threaded axially and internally and blockable by means of two external radial keep screws (43).

3. A system according to claim 1, wherein said directing piece has the shape of a prism with six faces, with an upper face having a gripping shank (55) extending therefrom.

4. A system according to claim 1, wherein said surgical patterns have an upper part (56) positionable above the bone and a lower part (57) introducible inside the bone, said upper and lower parts being located on both sides of a disk (58), said upper part having an orthohedric shape with a lateral face near to a cylindrical shank defining said lower part (57) terminating in the shape of an arrow head.

5. A system according to claim 1, wherein said tubular parts comprise retainers adapted for installation on a ball drill via a modified shank (68) of said ball drill.

6. A system according to claim 1, wherein said direction posts are straight (69) or angled (70) and are cylindrical with their ends of different diameters and permitting the control of direction, inclination and parallelism of drilling in the maxillary or mandibular bone.

* * * * *